United States Patent
Jung et al.

(10) Patent No.: US 9,527,898 B2
(45) Date of Patent: Dec. 27, 2016

(54) OXYNTOMODULIN DERIVATIVES AND PHARMACEUTICAL COMPOSITION FOR TREATING OBESITY COMPRISING THE SAME

(75) Inventors: Sung Youb Jung, Suwon-si (KR); Myung Hyun Jang, Seoul (KR); Ling Ai Shen, Seoul (KR); Young Kyung Park, Hwaseong-si (KR); Young Jin Park, Suwon-si (KR); Se Chang Kwon, Seoul (KR)

(73) Assignee: Hanmi Science Co., Ltd., Hawaseong-Si, Gyeonggi-Do (KR)

( * ) Notice: Subject to any disclaimer, the term of this patent is extended or adjusted under 35 U.S.C. 154(b) by 0 days.

(21) Appl. No.: 14/124,969

(22) PCT Filed: Jun. 7, 2012

(86) PCT No.: PCT/KR2012/004494
§ 371 (c)(1),
(2), (4) Date: Dec. 9, 2013

(87) PCT Pub. No.: WO2012/169798
PCT Pub. Date: Dec. 13, 2012

(65) Prior Publication Data
US 2014/0128318 A1    May 8, 2014

(30) Foreign Application Priority Data
Jun. 10, 2011 (KR) .......... 10-2011-0056472

(51) Int. Cl.
| | |
|---|---|
| *A61K 38/17* | (2006.01) |
| *C07K 14/705* | (2006.01) |
| *A61P 3/04* | (2006.01) |
| *C07K 14/575* | (2006.01) |
| *C07K 14/605* | (2006.01) |
| *A61K 45/06* | (2006.01) |
| *A61K 38/22* | (2006.01) |
| *A61K 38/00* | (2006.01) |

(52) U.S. Cl.
CPC .......... *C07K 14/575* (2013.01); *A61K 38/177* (2013.01); *A61K 38/22* (2013.01); *A61K 45/06* (2013.01); *C07K 14/605* (2013.01); *C07K 14/705* (2013.01); *A61K 38/00* (2013.01)

(58) Field of Classification Search
CPC ..... C07K 14/605; C07K 14/705; A61K 38/00; A61K 45/06; A61K 38/177
See application file for complete search history.

(56) References Cited

U.S. PATENT DOCUMENTS

| 7,217,845 | B2 | 5/2007 | Rosen et al. |
|---|---|---|---|
| 7,521,424 | B2 | 4/2009 | Rosen et al. |
| 7,737,260 | B2 | 6/2010 | Kim et al. |
| 7,928,058 | B2 | 4/2011 | Roy et al. |
| 8,263,084 | B2 | 9/2012 | Song et al. |
| 8,729,017 | B2 | 5/2014 | DiMarchi et al. |
| 8,778,872 | B2 | 7/2014 | DiMarchi et al. |
| 2004/0087778 | A1 | 5/2004 | Feige et al. |
| 2009/0238838 | A1 | 9/2009 | Kim et al. |
| 2009/0298757 | A1 | 12/2009 | Bloom et al. |
| 2010/0190701 | A1* | 7/2010 | Day et al. ........... 514/12 |
| 2010/0330108 | A1 | 12/2010 | Song et al. |
| 2011/0034374 | A1 | 2/2011 | Bloom et al. |
| 2012/0003712 | A1 | 1/2012 | Song et al. |
| 2012/0329707 | A1 | 12/2012 | DiMarchi et al. |
| 2013/0035285 | A1 | 2/2013 | Lau et al. |

FOREIGN PATENT DOCUMENTS

| CN | 101213209 A | 7/2008 |
|---|---|---|
| CN | 101389648 A | 3/2009 |
| CN | 101578107 A | 11/2009 |
| CN | 101974077 A | 2/2011 |
| CN | 102369209 A | 3/2012 |
| CN | 103732616 A | 4/2014 |
| CN | 103732618 A | 4/2014 |
| EP | 2300037 | 3/2011 |
| EP | 2330124 | 6/2011 |
| EP | 1891105 B1 | 4/2012 |
| JP | 2003-531632 A | 10/2003 |
| JP | 2008-543816 A | 12/2008 |
| JP | 2009-527558 A | 7/2009 |
| JP | 2009-203235 A | 9/2009 |
| JP | 2011-505355 A | 2/2011 |

(Continued)

OTHER PUBLICATIONS

Water, from http://www.biology-online.org/dictionary/Water, pp. 1-3, accessed Apr. 24, 2014.*
Rudinger, Peptide Hormones, JA Parsons, Ed., 1976, pp. 1-7.*
Sigma, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*

(Continued)

*Primary Examiner* — Julie Ha
*Assistant Examiner* — Li Ni Komatsu
(74) *Attorney, Agent, or Firm* — Baker & Hostetler LLP

(57) ABSTRACT

The present invention relates to a novel peptide showing more excellent activities on a glucagon like peptide-1 receptor and a glucagon receptor than native oxyntomodulin, and a composition for the prevention or treatment of obesity comprising the peptide as an active ingredient. Unlike native oxyntomodulin, the novel peptide of the present invention reduces food intake, suppresses gastric emptying, and facilitates lipolysis with reduced side-effects, and also shows excellent receptor-activating effects. Thus, it can be widely used in the treatment of obesity with safety and efficacy.

17 Claims, 1 Drawing Sheet

(56) References Cited

FOREIGN PATENT DOCUMENTS

| | | |
|---|---|---|
| JP | 2011-511753 A | 4/2011 |
| JP | 102010473 A | 4/2011 |
| JP | 2013-537525 A | 10/2013 |
| KR | 10-0389726 B1 | 6/2003 |
| KR | 10-2005-0026685 A | 3/2005 |
| KR | 1020060106486 A | 10/2006 |
| KR | 1020080039375 A | 5/2008 |
| KR | 10-2009-0096498 A | 9/2009 |
| KR | 1020090098843 A | 9/2009 |
| KR | 10-0925017 B1 | 10/2009 |
| KR | 10-2010-0105494 A | 9/2010 |
| KR | 1020100105494 A | 9/2010 |
| KR | 10-2011-0039230 A | 4/2011 |
| KR | 10-2012-0043208 A | 5/2012 |
| KR | 10-2012-0052973 A | 5/2012 |
| KR | 10-2012-0139579 A | 12/2012 |
| KR | 10-2014-0018462 | 2/2014 |
| TW | 200848423 A | 12/2008 |
| WO | 03/022304 A1 | 3/2003 |
| WO | 2005/035761 A1 | 4/2005 |
| WO | 2005087797 A1 | 9/2005 |
| WO | 2006/059106 A2 | 6/2006 |
| WO | 2006/134340 A2 | 12/2006 |
| WO | 2007/022123 A2 | 2/2007 |
| WO | 2007/100535 A2 | 9/2007 |
| WO | 2007/146038 A2 | 12/2007 |
| WO | 2008/071972 A1 | 6/2008 |
| WO | WO 2008/082274 A1 | 7/2008 |
| WO | 2008/101017 A2 | 8/2008 |
| WO | WO 2009/033756 A2 | 3/2009 |
| WO | WO 2009/058734 A1 | 5/2009 |
| WO | 2009/069983 A2 | 6/2009 |
| WO | 2009/099763 A1 | 8/2009 |
| WO | 2009/155257 A1 | 12/2009 |
| WO | WO 2009/155258 | 12/2009 |
| WO | 2010/013012 A2 | 2/2010 |
| WO | 2010/033207 A1 | 3/2010 |
| WO | 2010/033220 A2 | 3/2010 |
| WO | 2010/070253 A1 | 6/2010 |
| WO | 2010/071807 A1 | 6/2010 |
| WO | 2010/096052 A1 | 8/2010 |
| WO | 2010096142 A1 | 8/2010 |
| WO | 2010107256 A2 | 9/2010 |
| WO | WO 2010/108153 A2 | 9/2010 |
| WO | WO 2011/006497 A1 * | 1/2011 ........... C07K 14/605 |
| WO | WO 2011/056713 | 5/2011 |
| WO | WO 2011/071957 A1 | 6/2011 |
| WO | WO 2011/075393 A2 | 6/2011 |
| WO | WO 2011/087671 | 7/2011 |
| WO | WO 2011/087672 | 7/2011 |
| WO | WO 2011/143208 A1 | 11/2011 |
| WO | 2012011752 A2 | 1/2012 |
| WO | WO 2012/088379 A2 | 6/2012 |
| WO | 2012/169798 A2 | 12/2012 |
| WO | WO 2012/173422 | 12/2012 |
| WO | WO 2012/173422 A1 | 12/2012 |
| WO | WO 2013/157002 A1 | 10/2013 |
| WO | WO 2014/017843 | 1/2014 |
| WO | WO 2014/073842 | 5/2014 |

OTHER PUBLICATIONS

Obesity-Merck Manual, from http://www.merckmanuals.com/professional/nutritional_disorders/obesity_and_the_metab.., pp. 1-9, accessed Oct. 6, 2014.*
What Causes Overweight and Obesity?, from http://www.nhlbi.nih.gov/health/health-topics/topics/obe/causes.html, pp. 1-5, accessed Oct. 6, 2014.*
Obesity Causes, from http://www.hsph.harvard.edu/obesity-prevention-source/obesity-causes/, pp. 1-3, accessed Oct. 6, 2014.*
Prescription Medications for the Treatment of Obesity, pp. 1-8, published on Apr. 2013.*
Day et al, A new glucagon and GLP-1 co-agonist eliminates obesity in rodents, Nature Chemical Biology, 2009, 5, pp. 749-757.*
Taiwanese Patent Office, Communication dated Mar. 11, 2014, issued in corresponding Taiwanese Patent Application No. 101120633.
European Patent Office, Communication dated Dec. 3, 2014 issued in counterpart application No. 12797363.4.
European Patent Office, Communication dated Oct. 13, 2014, in application No. 12801247.3.
Wynne et al., "Oxyntomodulin increases energy expenditure in addition to decreasing energy intake in overweight and obese humans: a randomised controlled trial", International Journal of Obesity (2006) 30, 1729-1736.
Collie et al., "Purification and sequence of rat oxyntomodulin", Proc. Natl. Acad. Sci. USA, vol. 91, pp. 9362-9366, Sep. 1994.
U.S. Patent and Trademark Office, Communication dated Sep. 18, 2014, issued in U.S. Appl. No. 14/126,914.
State Intellectual Property Office of the P.R.C., Communication dated Jan. 7, 2015 issued in application No. 201280039781.4.
International Searching Authority, International Search Report and Written Opinion dated Nov. 14, 2012, issued in application No. PCT/KR2012/004722.
State Intellectual Property Office of the P.R.C., Communication dated Jan. 7, 2015, issued in corresponding Chinese Application No. 201280039781.4 (submitted without translation on May 1, 2015).
U.S. Patent and Trademark Office, Communication dated Jan. 13, 2016, issued in corresponding U.S. Appl. No. 14/748,389.
Drucker, Glucagon-Like Peptides, Diabetes, Feb. 1998, vol. 47, pp. 159-169.
Taiwanese Intellectual Property Office, Communication dated Dec. 23, 2013 issued in corresponding application No. 101121483.
Merriam Webster, Dictionary: prophylactic, (3 pages total), accessed from the WWW on Feb. 8, 2015. URL: http://www.merriam-webster.com/dictionary/prophylactic.
United States Patent and Trademark Office, Communication dated Mar. 5, 2015 issued in U.S. Appl. No. 14/126,914.
New Zealand Intellectual Property Office, Communication dated Oct. 30, 2015 issued in corresponding application No. 618810.
New Zealand Intellectual Property Office, Communication dated Oct. 7, 2014 issued in corresponding application No. 618810.
Japan Patent Office, English translation of Communication dated Dec. 15, 2015, issued in corresponding Japanese Application No. 2014-515759 (submitted without translation on Dec. 29, 2015).
Japan Patent Office, English translation of Communication dated Nov. 24, 2015, issued in corresponding Japanese Application No. 2014-514799 (submitted without translation on Dec. 29, 2015).
Federal Institute of Industrial Property, Communication dated Dec. 4, 2015, issued in corresponding Russian Application No. 2013153198/10.
Treetharnmathurot et al., "Effect of PEG molecular weight and linking chemistry on the biological activity and thermal stability of PEGylated trypsin", International Journal of Pharmaceutics, 2008, vol. 357, pp. 252-259.
Skosyrev et al., "The Dependence of Stability of the Green Fluorescent Protein-Obelin Hybrids on the Nature of Their Constituent Modules and the Structure of the Amino Acid Linker", Russian Journal of Bioorganic Chemistry, 2001, vol. 27, No. 5, pp. 323-329.
Federal Institute of Industrial Property, Communication dated Dec. 4, 2015, issued in corresponding Russian Application No. 2013154066/10.
Frankel et al., "Characterization of diphtheria fusion proteins targeted to the human interleukin-3 receptor", Protein Engineering, 2000, vol. 13, No. 8, pp. 575-581.
Korean Intellectual Property Office, Communication dated Aug. 28, 2014, issued in corresponding Korean Application No. 10-2012-0061166.
Korean Intellectual Property Office, Communication dated Sep. 30, 2013, issued in corresponding Korean Application No. 10-2012-0061166.
Korean Intellectual Property Office, Communication dated Nov. 20, 2014, issued in corresponding Korean Application No. 10-2012-0061166.

(56) References Cited

OTHER PUBLICATIONS

State Intellectual Property Office of PRC, English translation of communication dated Mar. 6, 2015, issued in corresponding Chinese Application No. 201280038851.4 (submitted without translation on May 1, 2015).

State Intellectual Property Office of PRC, English translation of communication dated Sep. 15, 2015, issued in corresponding Chinese Application No. 201280038851.4 (submitted without translation on Sep. 24, 2015).

Korean Intellectual Property Office, Communication dated Feb. 26, 2015, issued in corresponding Korean Application No. 10-2012-0061166.

English Translation of KR 20100105494 A, submitted Dec. 9, 2013.

Wynne et al, "Subcutaneous Oxyntomodulin Reduces Body Weight in Overweight and Obese Subjects A Double-Blind, Randomized, Controlled Trial", Diabetes, Aug. 2005, vol. 54, pp. 2390-2395.

U.S. Patent and Trademark Office, Communication dated Feb. 29, 2016, issued in co-pending U.S. Appl. No. 14/126,914.

"Vitamins & Supplements Search", http://www.webmd.com/vitamins-supplements/condition-1275-Hyperlipidemia.aspx, accessed Dec. 29, 2015, pp. 1-3.

Day et al., "A new glucagon and GLP-1 co-agonist eliminates obesity in rodents", Nature Chemical Biology, Oct. 2009, 5, 10, 749-757.

Day et al., "Optimization of Co-Agonism at GLP-1 and Glucagon Receptors to Safely Maximize Weight Reduction in DIO-Rodents", Peptide Science, 2012, 98, 443-450.

Ding et al., "Exendin-4, a Glucagon-Like Protein-1 (GLP-1) Receptor Agonist, Reverses Hepatic Steatosis in ob/ob Mice", Hepatology, 2006, 43, 173-181.

English translation of Japanese Patent Application No. 2014-515759: Notice of Reason for Rejection dated Dec. 15, 2015, 6 pages.

European Patent Application No. 13823727.6: Communication pursuant to Rule 164(1) EPC dated Feb. 25, 2016, 7 pages.

Goldberg, "Dyslipidemia", Dyslipidemia—Endocrine and Metabolic Disorders—Merck Manuals Professional Edition, http://www.merckmanuals.com/professional/endocrine-and-metabolic-diorders/lipid-dis . . . , accessed Dec. 29, 2015, 11 pages.

Hepatitis Health Center, "Fatty Liver Disease", http://www.webmd.com/hepatitis/fatty-liver-diseasepage=2&print=true, accessed Dec. 19, 2015, pp. 1-4.

International Patent Application No. PCT/KR2012/004722: International Search Report dated Nov. 14, 2012, 6 pages.

International Patent Application No. PCT/KR2013/006668: International Search Report and Written Opinion dated Oct. 21, 2013, 10 pages.

International Patent Application No. PCT/KR2013/009986: International Search Report and Written Opinion dated Jan. 29, 2014, 11 pages.

International Patent Application No. PCT/KR2013/009990: International Search Report and Written Opinion dated Jan. 20, 2014, 12 pages.

Lam, "Atherosclerosis", Atherosclerosis—Cardiovascular Disorders—Merck Manuals Professional Edition, http://www.merkmanuals.com/professional/cardiovascular-disorder/arteriosclerosis/atherosclerosis, accessed Dec. 29, 2015, 1-14.

Lam, "Definition of Arteriosclerosis", http://www.merkmanuals.com/professional/cardiovascular-disorders/arteriosclerosis/defi . . . , accessed Dec. 29, 2015, 1 page.

Lam, "Nonatheromatous Arteriosclerosis", http://222.merckmanuals.com/profession/cardiovasculardisorders/arteriosclerosis/non . . . , accessed Dec. 29, 2015, 2 pages.

Pocai et al., "Glucagon-like peptide 1/glucagon receptor dual agonism reverses obesity in mice", Diabetes, 2009, vol. 58, No. 10, 2253-2266.

Santoprete et al., "DPP-IV-resistant, long acting oxyntomodulin derivatives", Journal of Peptide Science, Feb. 2011, vol. 17, No. 4, 270-280.

Sigma-Aldrich, "Exendin-4 sequence", http://www.simgaaldrich.com/catalog/product/sigma/e7144lang=en®ion=US, accessed Dec. 28, 2015, 1 page.

U.S. Appl. No. 14/124,969: Communication dated Jun. 25, 2014, 12 pages.

U.S. Appl. No. 14/124,969: Final Rejection dated Apr. 14, 2015, 17 pages.

U.S. Appl. No. 14/124,969: Non-Final Rejection dated Dec. 10, 2014, 40 pages.

U.S. Appl. No. 14/415,200: Non-Final Rejection dated Jan. 20, 2016, 39 pages.

Vorobiev et al., "Chemical polysialylation: Design of conjugated human oxyntomodulin with a prolonged anorexic effect in vivo", Biochimie, 2013, vol. 95, 264-270.

\* cited by examiner

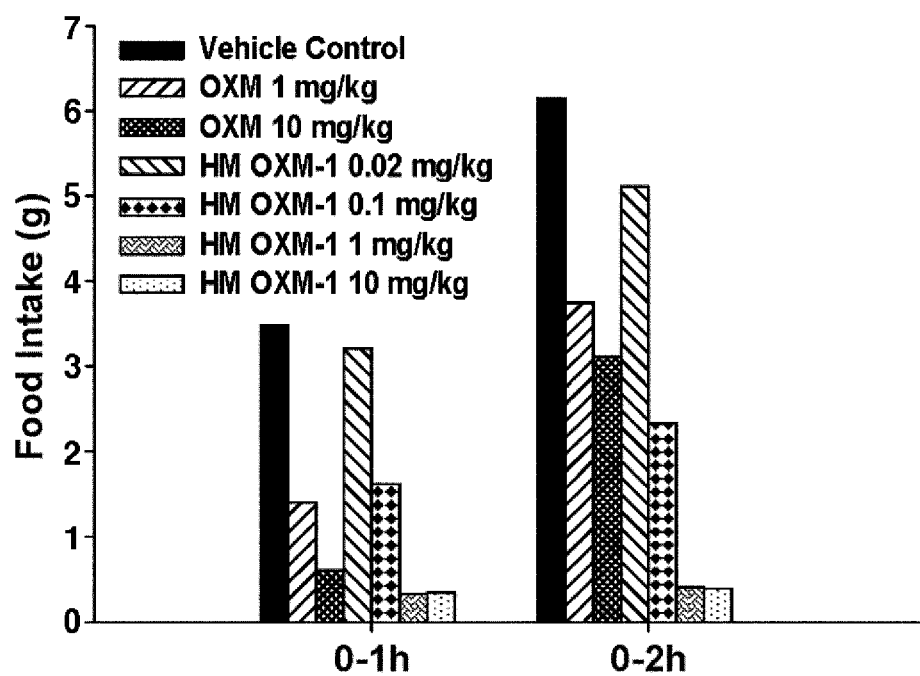

SEQUENCE LISTING

<160> NUMBER OF SEQ ID NOS: 56

<210> SEQ ID NO 1
<211> LENGTH: 37
<212> TYPE: PRT
<213> ORGANISM: Homo sapiens
<220> FEATURE:
<221> NAME/KEY: MISC_FEATURE
<222> LOCATION: (1)..(37)
<223> OTHER INFORMATION: Oxyntomodulin

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 2
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 2

His Ser Gln Gly Thr Phe Thr Ser Asp Tyr Ser Lys Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 3

His Ser Gln Gly Thr Phe Thr Ser Asp Tyr Ser Lys Tyr Leu Asp Glu
1               5                   10                  15

Arg Arg Ala Gln Asp Phe Val Ala Trp Leu Lys Asn Thr Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative

```
<220> FEATURE:
<221> NAME/KEY: MOD_RES
<222> LOCATION: (1)..(1)
<223> OTHER INFORMATION: 4-imidazoacetyl

<400> SEQUENCE: 4

His Gly Gln Gly Thr Phe Thr Ser Asp Tyr Ser Arg Tyr Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 5

His Gly Gln Gly Thr Phe Thr Ser Asp Tyr Ser Arg Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 6
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 6

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Lys Tyr Leu Asp
            35                  40

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 7
```

```
His Ser Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys
            20                  25                  30

<210> SEQ ID NO 8
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 8

His Ser Gln Gly Thr Phe Thr Ser Asp Leu Ser Arg Gln Leu Glu Glu
1               5                   10                  15

Glu Ala Val Arg Leu Phe Ile Glu Trp Leu Met Asn Lys
            20                  25

<210> SEQ ID NO 9
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid

<400> SEQUENCE: 9

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 10
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 10

His Ser Gln Gly Thr Phe Thr Ser Asp Tyr Ser Arg Gln Met Glu Glu
1               5                   10                  15

Glu Ala Val Arg Leu Phe Ile Glu Trp Leu Met Asn Gly Gly Pro Ser
            20                  25                  30

Ser Gly Ala Pro Pro Pro Ser Lys
        35                  40
```

<210> SEQ ID NO 11
<211> LENGTH: 43
<212> TYPE: PRT
<213> ORGANISM: Artificial Sequence
<220> FEATURE:
<223> OTHER INFORMATION: Description of Artificial Sequence: Synthetic polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 11

His Gly Glu Gly Thr Phe Thr Ser Asp Leu Ser Arg Gln Met Glu Glu
1               5                   10                  15

Glu Ala Val Arg Leu Phe Ile Glu Trp Ala Ala His Ser Gln Gly Thr
            20                  25                  30

Phe Thr Ser Asp Tyr Ser Arg Tyr Leu Asp Lys
        35                  40

<210> SEQ ID NO 12
<211> LENGTH: 38
<212> TYPE: PRT
<213> ORGANISM: Artificial Sequence
<220> FEATURE:
<223> OTHER INFORMATION: Description of Artificial Sequence: Synthetic polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 12

His Ser Gln Gly Thr Phe Thr Ser Asp Tyr Ser Arg Tyr Leu Asp Gly
1               5                   10                  15

Gly Gly His Gly Glu Gly Thr Phe Thr Ser Asp Leu Ser Lys Gln Met
            20                  25                  30

Glu Glu Glu Ala Val Lys
        35

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (16)..(16)
<223> OTHER INFORMATION: Alpha-methyl-glutamic acid
<220> FEATURE:
<221> NAME/KEY: MOD_RES
<222> LOCATION: (20)..(20)
<223> OTHER INFORMATION: Alpha-methyl-glutamic acid

<400> SEQUENCE: 13

His Ser Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys
            20                  25                  30

<210> SEQ ID NO 14

```
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (20)..(20)
<223> OTHER INFORMATION: Alpha-methyl-glutamic acid
<220> FEATURE:
<221> NAME/KEY: MOD_RES
<222> LOCATION: (24)..(24)
<223> OTHER INFORMATION: Alpha-methyl-glutamic acid

<400> SEQUENCE: 14

His Gly Gln Gly Thr Phe Thr Ser Asp Tyr Ser Arg Tyr Leu Asp Glu
1               5                   10                  15

Glu Ala Val Glu Leu Phe Ile Glu Trp Leu Met Asn Thr Lys Arg Asn
            20                  25                  30

Arg Asn Asn Ile Ala
        35

<210> SEQ ID NO 15
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (24)..(24)
<223> OTHER INFORMATION: Alpha-methyl-glutamic acid

<400> SEQUENCE: 15

His Gly Gln Gly Thr Phe Thr Ser Asp Tyr Ser Arg Tyr Leu Asp Glu
1               5                   10                  15

Glu Ala Val Arg Leu Phe Ile Glu Trp Leu Met Asn Thr Lys Arg Asn
            20                  25                  30

Arg Asn Asn Ile Ala
        35

<210> SEQ ID NO 16
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 16

His Ser Gln Gly Thr Phe Thr Ser Asp Leu Ser Arg Gln Leu Glu Gly
1               5                   10                  15

Gly Gly His Ser Gln Gly Thr Phe Thr Ser Asp Leu Ser Arg Gln Leu
            20                  25                  30
```

Glu Lys

<210> SEQ ID NO 17
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 17

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Thr Lys Arg Asn
            20                  25                  30

Arg Asn Asn Ile Ala
        35

<210> SEQ ID NO 18
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 18

His Ser Gln Gly Thr Phe Thr Ser Asp Tyr Ser Arg Tyr Leu Asp Glu
1               5                   10                  15

Glu Ala Val Arg Leu Phe Ile Glu Trp Ile Arg Asn Gly Gly Pro Ser
            20                  25                  30

Ser Gly Ala Pro Pro Pro Ser Lys
        35                  40

<210> SEQ ID NO 19
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 19

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Thr Lys Arg Asn
            20                  25                  30

Arg Asn Asn Ile Ala
        35

```
<210> SEQ ID NO 20
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MISC_FEATURE
<222> LOCATION: (16)..(20)
<223> OTHER INFORMATION: Ring formation between residues

<400> SEQUENCE: 20

His Ser Gln Gly Thr Phe Thr Ser Asp Tyr Ser Arg Tyr Leu Asp Glu
1               5                   10                  15

Glu Ala Val Lys Leu Phe Ile Glu Trp Ile Arg Asn Gly Gly Pro Ser
            20                  25                  30

Ser Gly Ala Pro Pro Pro Ser Lys
        35                  40

<210> SEQ ID NO 21
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: 4-imidazoacetyl

<400> SEQUENCE: 21

His Ser Gln Gly Thr Phe Thr Ser Asp Tyr Ser Arg Gln Leu Glu Glu
1               5                   10                  15

Glu Ala Val Arg Leu Phe Ile Glu Trp Val Arg Asn Thr Lys Arg Asn
            20                  25                  30

Arg Asn Asn Ile Ala
        35

<210> SEQ ID NO 22
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (1)..(1)
<223> OTHER INFORMATION: Desamino-histidyl
<220> FEATURE:
<221> NAME/KEY: MISC_FEATURE
<222> LOCATION: (16)..(20)
<223> OTHER INFORMATION: Ring formation between residues

<400> SEQUENCE: 22

His Ser Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Lys
            20                  25                  30

<210> SEQ ID NO 23
<211> LENGTH: 29
```

```
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 23

His Xaa Gln Gly Thr Phe Thr Ser Asp Tyr Ser Lys Tyr Leu Asp Glu
1               5                   10                  15

Lys Arg Ala Lys Glu Phe Val Cys Trp Leu Met Asn Thr
            20                  25

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 24

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 25

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (12)..(16)
```

<223> OTHER INFORMATION: Ring formation between residues

<400> SEQUENCE: 26

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 27
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 27

His Xaa Gln Gly Thr Phe Thr Ser Asp Tyr Ser Lys Tyr Leu Asp Glu
1               5                   10                  15

Gln Ala Ala Lys Glu Phe Ile Cys Trp Leu Met Asn Thr
            20                  25

<210> SEQ ID NO 28
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide construct of Oxyntomodulin derivative
<220> FEATURE:
<221> NAME/KEY: MOD_RES
<222> LOCATION: (2)..(2)
<223> OTHER INFORMATION: Aib

<400> SEQUENCE: 28

His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr
            20                  25

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (1)..(1)
<223> OTHER INFORMATION: 4-imidazoacetyl
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 29

```
His Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 30

His Xaa Gln Gly Thr Phe Thr Ser Asp Tyr Ala Lys Tyr Leu Asp Glu
1               5                   10                  15

Lys Arg Ala Lys Glu Phe Val Gln Trp Leu Met Asn Thr Cys
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide oxyntomodulin derivative
<220> FEATURE:
<221> NAME/KEY: MOD_RES
<222> LOCATION: (2)..(2)
<223> OTHER INFORMATION: Aib
<220> FEATURE:
<221> NAME/KEY: MISC_FEATURE
<222> LOCATION: (16)..(20)
<223> OTHER INFORMATION: Ring formation between residues

<400> SEQUENCE: 31

Tyr Xaa Gln Gly Thr Phe Thr Ser Asp Tyr Ser Lys Tyr Leu Asp Glu
1               5                   10                  15

Lys Arg Ala Lys Glu Phe Val Gln Trp Leu Met Asn Thr Cys
            20                  25                  30

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 32

Lys Arg Asn Arg Asn Asn Ile Ala
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct of group R2
```

```
<400> SEQUENCE: 33

Gly Pro Ser Ser Gly Ala Pro Pro Ser
1               5

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 34

Gly Pro Ser Ser Gly Ala Pro Pro Ser Lys
1               5                   10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 35

His Ser Gln Gly Thr Phe Thr Ser Asp Tyr Ser Lys Tyr Leu Asp
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 36

His Ser Gln Gly Thr Phe Thr Ser Asp Tyr Ser Arg Tyr Leu Asp Lys
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide construct of group R2

<400> SEQUENCE: 37

His Gly Glu Gly Thr Phe Thr Ser Asp Leu Ser Lys Gln Met Glu Glu
1               5                   10                  15

Glu Ala Val Lys
            20

<210> SEQ ID NO 38
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 38

Ser Gln Gly Thr Phe Thr Ser Asp Tyr Ser Lys Tyr Leu Asp Ser Arg
1               5                   10                  15

Arg Ala Gln Asp Phe Val Gln Trp Leu Met Asn Thr
```

```
            20                  25

<210> SEQ ID NO 39
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 39

Ser Gln Gly Thr Phe Thr Ser Asp Tyr Ser Lys Tyr Leu Asp Glu Glu
1               5                   10                  15

Ala Val Arg Leu Phe Ile Glu Trp Leu Met Asn Thr
            20                  25

<210> SEQ ID NO 40
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 40

Ser Gln Gly Thr Phe Thr Ser Asp Tyr Ser Lys Tyr Leu Asp Glu Arg
1               5                   10                  15

Arg Ala Gln Asp Phe Val Ala Trp Leu Lys Asn Thr
            20                  25

<210> SEQ ID NO 41
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 41

Gly Gln Gly Thr Phe Thr Ser Asp Tyr Ser Arg Tyr Leu Glu Glu Glu
1               5                   10                  15

Ala Val Arg Leu Phe Ile Glu Trp Leu Lys Asn Gly
            20                  25

<210> SEQ ID NO 42
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 42

Gly Gln Gly Thr Phe Thr Ser Asp Tyr Ser Arg Gln Met Glu Glu Glu
1               5                   10                  15

Ala Val Arg Leu Phe Ile Glu Trp Leu Lys Asn Gly
            20                  25

<210> SEQ ID NO 43
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide construct of group A or B
```

<400> SEQUENCE: 43

Gly Glu Gly Thr Phe Thr Ser Asp Leu Ser Arg Gln Met Glu Glu
1               5                   10                  15

Ala Val Arg Leu Phe Ile Glu Trp Ala Ala
            20                  25

<210> SEQ ID NO 44
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide construct of group A or B

<400> SEQUENCE: 44

Ser Gln Gly Thr Phe Thr Ser Asp Tyr Ser Arg Gln Met Glu Glu
1               5                   10                  15

Ala Val Arg Leu Phe Ile Glu Trp Leu Met Asn Gly
            20                  25

<210> SEQ ID NO 45
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 45

Gly Glu Gly Thr Phe Thr Ser Asp Leu Ser Arg Gln Met Glu Glu
1               5                   10                  15

Ala Val Arg Leu Phe Ile Glu Trp
            20

<210> SEQ ID NO 46
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide construct of group B

<400> SEQUENCE: 46

Ser Gln Gly Thr Phe Thr Ser Asp Tyr Ser Arg Tyr Leu Asp
1               5                   10

<210> SEQ ID NO 47
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
cccggccccc gcggccgcta ttcgaaatac                                    30

<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
gaacggtccg gaggacgtcg actcttaaga tag                              33
```

<210> SEQ ID NO 49
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
cagcgacacc gaccgtcccc ccgtacttaa ggcc                             34
```

<210> SEQ ID NO 50
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50

```
ctaaccgact ctcggggaag actgagctcg cc                               32
```

<210> SEQ ID NO 51
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Aib(aminosiobutyric acid), d-alanine, glycine,
      Sar(N-methylglycine), serine or d-serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)

```
<223> OTHER INFORMATION: Glutamic acid, serine, alpha-methyl-glutamic
      acid or not present
<220> FEATURE:
<221> NAME/KEY: MOD_RES
<222> LOCATION: (17)..(17)
<223> OTHER INFORMATION: Glutamine, glutamic acid, lysine, arginine,
      serine or not present
<220> FEATURE:
<221> NAME/KEY: MOD_RES
<222> LOCATION: (18)..(18)
<223> OTHER INFORMATION: Alanine, arginine, valine or not present
<220> FEATURE:
<221> NAME/KEY: MOD_RES
<222> LOCATION: (19)..(19)
<223> OTHER INFORMATION: Alanine, arginine, serine, valine or not
      present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, lysine,
      glutamine, alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, serine, valine
      or not present
<220> FEATURE:
<221> NAME/KEY: MOD_RES
<222> LOCATION: (27)..(27)
<223> OTHER INFORMATION: Alanine, lysine, methionine, glutamine,
      arginine or not present
<220> FEATURE:
<221> NAME/KEY: MISC_FEATURE
<222> LOCATION: (28)..(28)
<223> OTHER INFORMATION: May or may not be present
<220> FEATURE:
<221> NAME/KEY: MOD_RES
<222> LOCATION: (29)..(29)
<223> OTHER INFORMATION: Alanine, glycine, threonine or not present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MOD_RES
<222> LOCATION: (31)..(40)
<223> OTHER INFORMATION: Alanine, glycine, serine or not present
<220> FEATURE:
<221> NAME/KEY: MISC_FEATURE
<222> LOCATION: (31)..(40)
<223> OTHER INFORMATION: This region may encompass 2 to 10 amino acids,
      wherein some positions may be absent
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
```

"HSQGTFTSDYSKYLD" or "HSQGTFTSDYSRYLDK" or "HGEGTFTSDLSKQMEEEAVK,"
       wherein some or all positions may be absent
<220> FEATURE:
<223> OTHER INFORMATION: See specification as filed for detailed
      description of substitutions and preferred embodiments

<400> SEQUENCE: 51

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 52
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 26 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or "GQGTFTSDYSRYLEEEAVRLFIEWLKNG" or
      "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG,"
      wherein some positions may be absent
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 52

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa
        35                  40

<210> SEQ ID NO 53
<211> LENGTH: 59
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES -continued

```
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MISC_FEATURE
<222> LOCATION: (2)..(29)
<223> OTHER INFORMATION: This region may encompass 14 to 28 amino acids
      including "SQGTFTSDYSKYLDSRRAQDFVQWLMNT" or
      "SQGTFTSDYSKYLDEEAVRLFIEWLMNT" or "SQGTFTSDYSKYLDERRAQDFVAWLKNT"
      or
      "GQGTFTSDYSRYLEEEAVRLFIEWLKNG" or "GQGTFTSDYSRQMEEEAVRLFIEWLKNG"
<220> FEATURE:
<221> NAME/KEY: MISC_FEATURE
<222> LOCATION: (2)..(29)
<223> OTHER INFORMATION: Continued from above; or
      "GEGTFTSDLSRQMEEEAVRLFIEWAA" or "SQGTFTSDYSRQMEEEAVRLFIEWLMNG" or
      "GEGTFTSDLSRQMEEEAVRLFIEW" or "SQGTFTSDYSRYLD," wherein some
      positions may be absent
<220> FEATURE:
<221> NAME/KEY: MOD_RES
<222> LOCATION: (30)..(39)
<223> OTHER INFORMATION: Alanine, glycine, serine or not present
<220> FEATURE:
<221> NAME/KEY: MISC_FEATURE
<222> LOCATION: (30)..(39)
<223> OTHER INFORMATION: This region may encompass 2 to 10 amino acids,
      wherein some positions may be absent
<220> FEATURE:
<221> NAME/KEY: MISC_FEATURE
<222> LOCATION: (40)..(59)
<223> OTHER INFORMATION: This region may encompass 15 to 20 amino acids
      including "HSQGTFTSDYSKYLD" or "HSQGTFTSDYSRYLDK" or
      "HGEGTFTSDLSKQMEEEAVK," wherein some positions may be absent
<220> FEATURE:
<223> OTHER INFORMATION: See specification as filed for detailed
      description of substitutions and preferred embodiments

<400> SEQUENCE: 53

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa
    50                  55

<210> SEQ ID NO 54
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (16)..(16)
<223> OTHER INFORMATION: Serine, glutamic acid or arginine
<220> FEATURE:
<221> NAME/KEY: MOD_RES
<222> LOCATION: (17)..(17)
<223> OTHER INFORMATION: Arginine, glutamic acid or serine
<220> FEATURE:
<221> NAME/KEY: MOD_RES
<222> LOCATION: (18)..(18)
<223> OTHER INFORMATION: Arginine, alanine or valine
<220> FEATURE:
```

```
<221> NAME/KEY: MOD_RES
<222> LOCATION: (19)..(19)
<223> OTHER INFORMATION: Arginine, valine or serine
<220> FEATURE:
<221> NAME/KEY: MOD_RES
<222> LOCATION: (20)..(20)
<223> OTHER INFORMATION: Glutamine, arginine or lysine
<220> FEATURE:
<221> NAME/KEY: MOD_RES
<222> LOCATION: (26)..(26)
<223> OTHER INFORMATION: Isoleucine, valine or serine
<220> FEATURE:
<221> NAME/KEY: MOD_RES
<222> LOCATION: (27)..(27)
<223> OTHER INFORMATION: Methionine, arginine or glutamine
<220> FEATURE:
<221> NAME/KEY: MOD_RES
<222> LOCATION: (29)..(29)
<223> OTHER INFORMATION: Threonine, glycine or alanine
<220> FEATURE:
<221> NAME/KEY: MISC_FEATURE
<222> LOCATION: (30)..(40)
<223> OTHER INFORMATION: This region may encompass 8 to 11 amino acids
      including "KRNRNNIA" or "GPSSGAPPPS" or "GPSSGAPPPSK," wherein
      some positions may be absent
<220> FEATURE:
<223> OTHER INFORMATION: See specification as filed for detailed
      description of substitutions and preferred embodiments

<400> SEQUENCE: 54

Xaa Ser Gln Gly Thr Phe Thr Ser Asp Tyr Ser Lys Tyr Leu Asp Xaa
1               5                   10                  15

Xaa Xaa Xaa Xaa Leu Phe Val Gln Trp Xaa Xaa Asn Xaa Xaa Xaa Xaa
            20                  25                  30

Xaa Xaa Xaa Xaa Xaa Xaa Xaa Xaa
        35                  40

<210> SEQ ID NO 55
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, dimethyl-histidyl
      (N-dimethyl-histidyl), beta-hydroxyimidazopropionyl,
      4-imidazoacetyl, beta-carboxy imidazopropionyl or tyrosine
<220> FEATURE:
<221> NAME/KEY: MOD_RES
<222> LOCATION: (2)..(2)
<223> OTHER INFORMATION: Serine, Aib, Sar, d-alanine or d-serine
<220> FEATURE:
<221> NAME/KEY: MOD_RES
<222> LOCATION: (16)..(16)
<223> OTHER INFORMATION: Serine or glutamic acid
<220> FEATURE:
<221> NAME/KEY: MOD_RES
<222> LOCATION: (17)..(17)
<223> OTHER INFORMATION: Arginine or lysine
<220> FEATURE:
<221> NAME/KEY: MOD_RES
<222> LOCATION: (20)..(20)
<223> OTHER INFORMATION: Glutamine or lysine
<220> FEATURE:
<221> NAME/KEY: MOD_RES
<222> LOCATION: (21)..(21)
<223> OTHER INFORMATION: Aspartic acid or glutamic acid
<220> FEATURE:
<221> NAME/KEY: MOD_RES
<222> LOCATION: (24)..(24)
<223> OTHER INFORMATION: Glutamine, cysteine or lysine
<220> FEATURE:
```

```
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(41)
<223> OTHER INFORMATION: This region may encompass 8 to 11 amino acids
      including "KRNRNNIA" or "GPSSGAPPPS" or "GPSSGAPPPSK," wherein
      some or all positions may be absent
<220> FEATURE:
<223> OTHER INFORMATION: See specification as filed for detailed
      description of substitutions and preferred embodiments

<400> SEQUENCE: 55

Xaa Xaa Gln Gly Thr Phe Thr Ser Asp Tyr Ser Lys Tyr Leu Asp Xaa
1               5                   10                  15

Xaa Arg Ala Xaa Xaa Phe Val Xaa Trp Leu Met Asn Thr Xaa Xaa Xaa
            20                  25                  30

Xaa Xaa Xaa Xaa Xaa Xaa Xaa Xaa Xaa
            35                  40

<210> SEQ ID NO 56
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Histidine, desamino-histidyl, 4-imidazoacetyl
      or tyrosine
<220> FEATURE:
<221> NAME/KEY: MOD_RES
<222> LOCATION: (2)..(2)
<223> OTHER INFORMATION: Aib(aminosiobutyric acid), glycine or serine
<220> FEATURE:
<221> NAME/KEY: MOD_RES
<222> LOCATION: (3)..(3)
<223> OTHER INFORMATION: Glutamic acid or glutamine
<220> FEATURE:
<221> NAME/KEY: MOD_RES
<222> LOCATION: (10)..(10)
<223> OTHER INFORMATION: Leucine or tyrosine
<220> FEATURE:
<221> NAME/KEY: MOD_RES
<222> LOCATION: (11)..(11)
<223> OTHER INFORMATION: Serine or alanine
<220> FEATURE:
<221> NAME/KEY: MOD_RES
<222> LOCATION: (12)..(12)
<223> OTHER INFORMATION: Lysine or arginine
<220> FEATURE:
<221> NAME/KEY: MOD_RES
<222> LOCATION: (13)..(13)
<223> OTHER INFORMATION: Glutamine or tyrosine
<220> FEATURE:
<221> NAME/KEY: MOD_RES
<222> LOCATION: (14)..(14)
<223> OTHER INFORMATION: Leucine or methionine
<220> FEATURE:
<221> NAME/KEY: MOD_RES
<222> LOCATION: (15)..(15)
<223> OTHER INFORMATION: Aspartic acid or glutamic acid
<220> FEATURE:
<221> NAME/KEY: MOD_RES
<222> LOCATION: (16)..(16)
<223> OTHER INFORMATION: Glutamic acid, alpha-methyl-glutamic acid or
      not present
<220> FEATURE:
<221> NAME/KEY: MOD_RES
<222> LOCATION: (17)..(17)
<223> OTHER INFORMATION: Glutamine, glutamic acid, lysine, arginine or
      not present
```

```
<220> FEATURE:
<221> NAME/KEY: MOD_RES
<222> LOCATION: (18)..(18)
<223> OTHER INFORMATION: Alanine, arginine or not present
<220> FEATURE:
<221> NAME/KEY: MOD_RES
<222> LOCATION: (19)..(19)
<223> OTHER INFORMATION: Alanine, valine or not present
<220> FEATURE:
<221> NAME/KEY: MOD_RES
<222> LOCATION: (20)..(20)
<223> OTHER INFORMATION: Lysine, glutamine, arginine, alpha-methyl-
      glutamic acid or not present
<220> FEATURE:
<221> NAME/KEY: MOD_RES
<222> LOCATION: (21)..(21)
<223> OTHER INFORMATION: Aspartic acid, glutamic acid, leucine or not
      present
<220> FEATURE:
<221> NAME/KEY: MISC_FEATURE
<222> LOCATION: (22)..(22)
<223> OTHER INFORMATION: May or may not be present
<220> FEATURE:
<221> NAME/KEY: MOD_RES
<222> LOCATION: (23)..(23)
<223> OTHER INFORMATION: Isoleucine, valine or not present
<220> FEATURE:
<221> NAME/KEY: MOD_RES
<222> LOCATION: (24)..(24)
<223> OTHER INFORMATION: Alanine, cysteine, glutamic acid, glutamine,
      alpha-methyl-glutamic acid or not present
<220> FEATURE:
<221> NAME/KEY: MISC_FEATURE
<222> LOCATION: (25)..(25)
<223> OTHER INFORMATION: May or may not be present
<220> FEATURE:
<221> NAME/KEY: MOD_RES
<222> LOCATION: (26)..(26)
<223> OTHER INFORMATION: Alanine, isoleucine, leucine, valine or not
      present
<220> FEATURE:
<221> NAME/KEY: MOD_RES
<222> LOCATION: (27)..(27)
<223> OTHER INFORMATION: Alanine, lysine, methionine, arginine or not
      present
<220> FEATURE:
<221> NAME/KEY: MISC_FEATURE
<222> LOCATION: (28)..(29)
<223> OTHER INFORMATION: May or may not be present
<220> FEATURE:
<221> NAME/KEY: MOD_RES
<222> LOCATION: (30)..(30)
<223> OTHER INFORMATION: Cysteine, lysine or not present
<220> FEATURE:
<221> NAME/KEY: MISC_FEATURE
<222> LOCATION: (31)..(40)
<223> OTHER INFORMATION: This region may encompass 2 to 10 residues,
      wherein some positions may not be present
<220> FEATURE:
<221> NAME/KEY: MISC_FEATURE
<222> LOCATION: (41)..(60)
<223> OTHER INFORMATION: This region may encompass 8 to 20 amino acids
      including "KRNRNNIA" or "GPSSGAPPPS" or "GPSSGAPPPSK" or
      "HSQGTFTSDYSKYLD" or "HSQGTFTSDYSRYLDK" or "HGEGTFTSDLSKQMEEEAVK,"
      wherein some or all positions may be absent
<220> FEATURE:
<223> OTHER INFORMATION: See specification as filed for detailed
      description of substitutions and preferred embodiments

<400> SEQUENCE: 56

Xaa Xaa Xaa Gly Thr Phe Thr Ser Asp Xaa Xaa Xaa Xaa Xaa Xaa
1               5                   10                  15

Xaa Xaa Xaa Xaa Xaa Phe Xaa Xaa Trp Xaa Xaa Asn Thr Xaa Gly Gly
                20                  25                  30

Gly Gly Gly Gly Gly Gly Gly Xaa Xaa Xaa Xaa Xaa Xaa Xaa Xaa
        35                  40                  45
```

```
Xaa Xaa Xaa Xaa Xaa Xaa Xaa Xaa Xaa Xaa Xaa Xaa
 50                  55                  60
```

OXYNTOMODULIN DERIVATIVES AND PHARMACEUTICAL COMPOSITION FOR TREATING OBESITY COMPRISING THE SAME

CROSS REFERENCE TO RELATED APPLICATIONS

This application is a National Stage of International Application No. PCT/KR2012/004494, filed on Jun. 7, 2012, claiming priority based on Korean Patent Application No. 10-2011-0056472, filed Jun. 10, 2011 the content of all of which are incorporated herein by reference in their entirety.

TECHNICAL FIELD

The present invention relates to a novel peptide showing excellent activities on a glucagon like peptide-1 receptor and a glucagon receptor greater than native oxyntomodulin, and a composition for the prevention or treatment of obesity comprising the peptide as an active ingredient.

BACKGROUND ART

Recently, economic growth and changes in lifestyle are leading to changes in eating habits. The main causes of rising overweight and obesity rates in contemporary people are consumption of high-calorie foods such as fast foods and lack of exercise. World Health Organization (WHO) estimates that more than 1 billion people worldwide are overweight and at least 300 million of them are clinically obese. In particular, 250,000 people die each year in Europe and more than 2.5 million people worldwide die each year as a result of being overweight (World Health Organization, Global Strategy on Diet, Physical Activity and Health, 2004).

Being overweight and obese increases blood pressure and cholesterol levels to cause occurrence or exacerbation of various diseases such as cardiovascular disease, diabetes, and arthritis, and are also main causes of rising incidence rates of arteriosclerosis, hypertension, hyperlipidemia or cardiovascular disease in children or adolescents as well as in adults.

Obesity is a severe condition that causes various diseases worldwide. It is thought to be overcome by individual efforts, and it is also believed that obese patients lack self-control. However, it is difficult to treat obesity, because obesity is a complex disorder involving appetite regulation and energy metabolism. For the treatment of obesity, abnormal actions associated with appetite regulation and energy metabolism should be treated together with efforts of obese patients. Many attempts have been made to develop drugs capable of treating the abnormal actions. As the result of these efforts, drugs such as Rimonabant (Sanofi-Aventis), Sibutramin (Abbott), Contrave (Takeda), and Orlistat (Roche) have been developed, but they have the disadvantages of serious adverse effects or very weak anti-obesity effects. For example, it was reported that Rimonabant (Sanofi-Aventis) shows a side-effect of central nerve disorder, Sibutramine (Abbott) and Contrave (Takeda) show cardiovascular side-effects, and Orlistat (Roche) shows only 4 kg of weight loss when taken for 1 year. Unfortunately, there are no therapeutic agents for obesity which can be safely prescribed for obese patients.

Many studies have been made to develop therapeutic agents for obesity which do not have the problems of the conventional anti-obesity drugs. Recently, glucagon derivatives have received much attention. Glucagon is produced by the pancreas when the level of glucose in the blood drops resulting from other medications or diseases, hormone or enzyme deficiencies. Glucagon stimulates glycogen breakdown in the liver, and facilitates glucose release to raise blood glucose levels to a normal range. In addition to the effect of increasing the blood glucose level, glucagon suppresses appetite and activates hormone-sensitive lipase (HSL) of adipocytes to facilitate lipolysis, thereby showing anti-obesity effects. One of the glucagon derivatives, glucagon like peptide-1 (GLP-1) is under development as a therapeutic agent for hyperglycemia in patients with diabetes, and it functions to stimulate insulin synthesis and secretion, to inhibit glucagon secretion, to slow gastric emptying, to increase glucose utilization, and to inhibit food intake. Exendin-4 is isolated from lizard venom that shares approximately 50% amino acid homology with GLP-1 and is also reported to activate the GLP-1 receptor, thereby ameliorating hyperglycemia in patients with diabetes. However, anti-obesity drugs including GLP-1 are reported to show side-effects such as vomiting and nausea.

As an alternative to GLP-1, therefore, much attention has been focused on oxyntomodulin, a peptide derived from a glucagon precursor, pre-glucagon that binds to the receptors of two peptides, GLP-1 and glucagon. Oxyntomodulin represents a potent anti-obesity therapy, because it inhibits food intake like GLP-1, promotes satiety, and has a lipolytic activity like glucagon.

Based on the dual function of the oxyntomodulin peptide, it has been actively studied as a drug for the treatment of obesity. For example, Korean Patent No. 925017 discloses a pharmaceutical composition including oxyntomodulin as an active ingredient for the treatment of overweight human, which is administered via an oral, parenteral, mucosal, rectal, subcutaneous, or transdermal route. However, it has been reported that this anti-obesity drug including oxyntomodulin has a short in vivo half-life and weak therapeutic efficacy, even though administered at a high dose three times a day. Thus, many efforts have been made to improve the in vivo half-life or therapeutic effect of oxyntomodulin on obesity by its modification.

For example, a dual agonist oxyntomodulin (Merck) is prepared by substituting L-serine with D-serine at position 2 of oxyntomodulin to increase a resistance to dipeptidyl peptidase-IV (DPP-IV) and by attaching a cholesterol moiety at the C-terminal to increase the blood half-life at the same time. ZP2929 (Zealand) is prepared by substituting L-serine with D-serine at position 2 to enhance resistance to DPP-IV, substituting arginine with alanine at position 17 to enhance resistance to protease, substituting methionine with lysine at position 27 to enhance oxidative stability, and substituting glutamine with aspartic acid and alanine at positions 20 and 24 and asparagine with serine at position 28 to enhance deamidation stability. However, even though the half-life of the dual agonist oxyntomodulin (Merck) was enhanced to show half-life 8-12 minutes longer than the native oxyntomodulin, it still has a very short in vivo half-life of 1.7 hr and its administration dose is also as high as several mg/kg. Unfortunately, oxyntomodulin or derivatives thereof have disadvantages of daily administration of high dose due to the short half-life and low efficacy.

DISCLOSURE

Technical Problem

Accordingly, the present inventors have developed an oxyntomodulin derivative prepared by modifying the amino acid sequence of native oxyntomodulin in order to enhance its therapeutic effects on obesity and to reduce its administration dose. As a result, they found that the oxyntomodulin derivative shows more excellent activities on a glucagon receptor and a GLP-1 receptor than native oxyntomodulin, thereby completing the present invention.

Technical Solution

An object of the present invention is to provide a novel peptide showing excellent therapeutic effects on obesity. Another object of the present invention is to provide a composition for the prevention or treatment of obesity, comprising the peptide. Still another object of the present invention is to provide a method for preventing or treating obesity by administering the peptide or the composition to a subject.

Still another object of the present invention is to provide use of the peptide in the preparation of drugs for the prevention or treatment of obesity.

Advantageous Effects

Unlike native oxyntomodulin, the novel peptide of the present invention reduces food intake, suppresses gastric emptying, and facilitates lipolysis without side-effects, and also shows excellent receptor-activating effects. Thus, it can be widely used in the treatment of obesity with safety and efficacy.

DESCRIPTION OF DRAWINGS

FIG. 1 is a graph showing changes in food intake according to administration dose of oxyntomodulin or oxyntomodulin derivative.

BEST MODE

In one aspect to achieve the above objects, the present invention provides a novel peptide including the amino acid sequence of the following Formula 1.

R1-X1-X2-GTFTSD-X3-X4-X5-X6-X7-X8-X9-X10-
X11-X12-X13-X14-X15-X16-X17-X18-X19-
X20-X21-X22-X23-X24-R2 (SEQ ID NO: 51)    (Formula 1)

wherein R1 is histidine, desamino-histidyl, dimethyl-histidyl(N-dimethyl-histidyl), beta-hydroxyimidazopropionyl, 4-imidazoacetyl, beta-carboxy imidazopropionyl or tyrosine;

X1 is Aib(aminoisobutyric acid), d-alanine, glycine, Sar (N-methylglycine), serine, or d-serine;

X2 is glutamic acid or glutamine;
X3 is leucine or tyrosine;
X4 is serine or alanine;
X5 is lysine or arginine;
X6 is glutamine or tyrosine;
X7 is leucine or methionine;
X8 is aspartic acid or glutamic acid;
X9 is glutamic acid, serine, alpha-methyl-glutamic acid or is deleted;
X10 is glutamine, glutamic acid, lysine, arginine, serine or is deleted;
X11 is alanine, arginine, valine or is deleted;
X12 is alanine, arginine, serine, valine or is deleted;
X13 is lysine, glutamine, arginine, alpha-methyl-glutamic acid or is deleted;
X14 is aspartic acid, glutamic acid, leucine or is deleted;
X15 is phenylalanine or is deleted;
X16 is isoleucine, valine or is deleted;
X17 is alanine, cysteine, glutamic acid, lysine, glutamine, alpha-methyl-glutamic acid or is deleted;
X18 is tryptophan or is deleted;
X19 is alanine, isoleucine, leucine, serine, valine or is deleted;
X20 is alanine, lysine, methionine, glutamine, arginine or is deleted;
X21 is asparagine or is deleted;
X22 is alanine, glycine, threonine or is deleted;
X23 is cysteine, lysine or is deleted;
X24 is a peptide having 2 to 10 amino acids consisting of combinations of alanine, glycine and serine, or is deleted; and
R2 is KRNRNNIA (SEQ ID NO. 32), GPSSGAPPPS (SEQ ID NO. 33), GPSSGAPPPSK (SEQ ID NO. 34), HSQGTFTSDYSKYLD (SEQ ID NO. 35), HSQGTFTSDYSRYLDK (SEQ ID NO. 36), HGEGTFTSDLSKQMEEEAVK (SEQ ID NO. 37) or is deleted (excluded if the amino acid sequence of Formula 1 is identical to that of SEQ ID NO. 1).

As used herein, the term "peptide" means a compound of two or more α-amino acids linked by a peptide bond. With respect to the objects of the present invention, it means a peptide that activates both the GLP-1 receptor and the glucagon receptor to show anti-obesity effects. The peptide according to the present invention includes peptides, peptide derivatives or peptide mimetics that are prepared by addition, deletion or substitution of amino acids of oxyntomodulin so as to activate both of the GLP-1 receptor and the glucagon receptor at a high level, compared to the native oxyntomodulin.

Amino acids mentioned herein are abbreviated according to the nomenclature rule of IUPAC-IUB as follows:

| Alanine | A | Arginine | R |
| Asparagine | N | Aspartic acid | D |
| Cysteine | C | Glutamic acid | E |
| Glutamine | Q | Glycine | G |
| Histidine | H | Isoleucine | I |
| Leucine | L | Lysine | K |
| Methionine | M | Phenylalanine | F |
| Proline | P | Serine | S |
| Threonine | T | Tryptophan | W |
| Tyrosine | Y | Valine | V |

In the present invention, the peptide encompasses any peptide that is prepared by substitutions, additions, deletions or post translational modifications (e.g., methylation, acylation, ubiquitination, intramolecular covalent bonding) in the amino acid sequence of oxyntomodulin (HSQGTFTSDYSKYLDSRRAQDFVQWLMNTKRNRNNIA, SEQ ID NO. 1) so as to activate the glucagon and GLP-1 receptors at the same time. Upon substitution or addition of amino acids, any of the 20 amino acids commonly found in human proteins, as well as atypical or non-naturally occurring amino acids can be used. Commercially available sources of atypical amino acids include Sigma-Aldrich, ChemPep Inc., and Genzyme Pharmaceuticals. The peptides including these amino acids and atypical peptide sequences may be synthesized and purchased from commercial suppliers, for example, American Peptide Company or Bachem (USA) or Anygen (Korea).

In order to enhance the activity of the wild-type oxyntomodulin for the glucagon receptor and the GLP-1 receptor, the peptide of the present invention may be substituted with 4-imidazoacetyl where the alpha carbon of histidine at position 1 of amino acid sequence represented by SEQ ID NO. 1 is deleted, desamino-histidyl where the N-terminal amino group is deleted, dimethyl-histidyl (N-dimethyl-histidyl) where the N-terminal amino group is modified with two methyl groups, beta-hydroxy imidazopropionyl where the N-terminal amino group is substituted with a hydroxyl group, or beta-carboxy imidazopropionyl where the N-terminal amino group is substituted with a carboxyl group. In addition, the GLP-1 receptor-binding region may be substituted with amino acids that enhance hydrophobic and ionic bonds or combinations thereof. Apart of the oxyntomodulin sequence may be substituted with the amino acid sequence of GLP-1 or Exendin-4 to enhance the activity on GLP-1 receptor.

Further, a part of the oxyntomodulin sequence may be substituted with a sequence stabilizing alpha helix. Preferably, amino acids at positions 10, 14, 16, 20, 24 and 28 of the amino acid sequence of Formula 1 may be substituted with amino acids or amino acid derivatives consisting of Tyr(4-Me), Phe, Phe(4-Me), Phe(4-Cl), Phe(4-CN), Phe(4-NO$_2$), Phe(4-NH$_2$), Phg, Pal, Nal, Ala(2-thienyl) and Ala (benzothienyl) that are known to stabilize alpha helix, and there are no limitations on the type and number of alpha helix-stabilizing amino acid or amino acid derivatives to be inserted. Preferably, amino acids at positions 10 and 14, 12 and 16, 16 and 20, 20 and 24, and 24 and 28 may be also substituted with glutamic acid or lysine, respectively so as to form rings, and there is no limitation on the number of rings to be inserted. Most preferably, the peptide may be a peptide having an amino acid sequence selected from the following Formulae 2 to 6.

In one specific embodiment, the peptide of the present invention is an oxyntomodulin derivative including the amino acid sequence of the following Formula 2 where the amino acid sequence of oxyntomodulin is substituted with that of exendin or GLP-1.

R1-A-R3 (SEQ ID NO: 52)        (Formula 2)

In another specific embodiment, the peptide of the present invention is an oxyntomodulin derivative including the amino acid sequence of the following Formula 3, which is prepared by linking a part of the amino acid sequence of oxyntomodulin and a part of the amino acid sequence of exendin or GLP-1 via a proper amino acid linker.

R1-B-C-R4 (SEQ ID NO: 53)        (Formula 3)

In still another specific embodiment, the peptide of the present invention is an oxyntomodulin derivative including the amino acid sequence of the following Formula 4, wherein a part of the amino acid sequence of oxyntomodulin is substituted with an amino acid capable of enhancing the binding affinity to GLP-1 receptor, for example, Leu at position 26 which binds with GLP-1 receptor by hydrophobic interaction is substituted with the hydrophobic residue, Ile or Val.

(Formula 4)
R1-SQGTFTSDYSKYLD-D1-D2-D3-D4-D5-LFVQW-D6-D7-N-
D8-R3 (SEQ ID NO: 54)

In still another specific embodiment, the peptide of the present invention is an oxyntomodulin derivative including the following Formula 5, wherein a part of the amino acid sequence is deleted, added, or substituted with other amino acid in order to enhance the activities of native oxyntomodulin on GLP-1 receptor and glucagon receptor.

(Formula 5)
R1-E1-QGTFTSDYSKYLD-E2-E3-RA-E4-E5-FV-E6-WLMNT-
E7-R5 (SEQ ID NO: 55)

In Formulae 2 to 5, R1 is the same as in the description of Formula 1;

A is selected from the group consisting of SQGTFTSDYSKYLDSRRAQDFVQWLMNT (SEQ ID NO. 38), SQGTFTSDYSKYLDEEAVRLFIEWLMNT (SEQ ID NO. 39), SQGTFTSDYSKYLDERRAQDFVAWLKNT (SEQ ID NO. 40), GQGTFTSDYSRYLEEEAVRLFIEWLKNG (SEQ ID NO. 41), GQGTFTSDYSRQMEEEAVRLFIEWLKNG (SEQ ID NO. 42), GEGTFTSDLSRQMEEEAVRLFIEWAA (SEQ ID NO. 43), and SQGTFTSDYSRQMEEEAVRLFIEWLMNG (SEQ ID NO. 44);

B is selected from the group consisting of SQGTFTSDYSKYLDSRRAQDFVQWLMNT (SEQ ID NO. 38), SQGTFTSDYSKYLDEEAVRLFIEWLMNT (SEQ ID NO. 39), SQGTFTSDYSKYLDERRAQDFVAWLKNT (SEQ ID NO. 40), GQGTFTSDYSRYLEEEAVRLFIEWLKNG (SEQ ID NO. 41), GQGTFTSDYSRQMEEEAVRLFIEWLKNG (SEQ ID NO. 42), GEGTFTSDLSRQMEEEAVRLFIEWAA (SEQ ID NO. 43), SQGTFTSDYSRQMEEEAVRLFIEWLMNG (SEQ ID NO. 44), GEGTFTSDLSRQMEEEAVRLFIEW (SEQ ID NO. 45), and SQGTFTSDYSRYLD (SEQ ID NO. 46);

C is a peptide having 2 to 10 amino acids consisting of combinations of alanine, glycine and serine;
D1 is serine, glutamic acid or arginine;
D2 is arginine, glutamic acid or serine;
D3 is arginine, alanine or valine;
D4 is arginine, valine or serine;
D5 is glutamine, arginine or lysine;
D6 is isoleucine, valine or serine;
D7 is methionine, arginine or glutamine;
D8 is threonine, glycine or alanine;
E1 is serine, Aib, Sar, d-alanine or d-serine;
E2 is serine or glutamic acid;
E3 is arginine or lysine;
E4 is glutamine or lysine;
E5 is aspartic acid or glutamic acid;
E6 is glutamine, cysteine or lysine;
E7 is cysteine, lysine or is deleted;
R3 is KRNRNNIA (SEQ ID NO: 32), GPSSGAPPPS (SEQ ID NO: 33) or GPSSGAPPPSK (SEQ ID NO: 34);
R4 is HSQGTFTSDYSKYLD (SEQ ID NO. 35), HSQGTFTSDYSRYLDK (SEQ ID NO. 36) or HGEGTFTSDLSKQMEEEAVK (SEQ ID NO. 37); and,
R5 is KRNRNNIA (SEQ ID NO. 32), GPSSGAPPPS (SEQ ID NO. 33), GPSSGAPPPSK (SEQ ID NO. 34) or is deleted (excluded if the amino acid sequences of Formula 2 to 5 are identical to that of SEQ ID NO. 1).

Preferably, the novel peptide of the present invention may be a peptide of the following Formula 6.

R1-X1-X2-GTFTSD-X3-X4-X5-X6-X7-X8-X9-X10-
X11-X12-X13-X14-X15-X16-X17-X18-X19-
X20-X21-X22-X23-X24-R2 (SEQ ID NO: 56)    (Formula 6)

wherein R1 is histidine, desamino-histidyl, 4-imidazoacetyl or tyrosine;
X1 is Aib(aminoisobutyric acid), glycine or serine;
X2 is glutamic acid or glutamine;
X3 is leucine or tyrosine;
X4 is serine or alanine;
X5 is lysine or arginine;

X6 is glutamine or tyrosine;
X7 is leucine or methionine;
X8 is aspartic acid or glutamic acid;
X9 is glutamic acid, alpha-methyl-glutamic acid or is deleted;
X10 is glutamine, glutamic acid, lysine, arginine or is deleted;
X11 is alanine, arginine or is deleted;
X12 is alanine, valine or is deleted;
X13 is lysine, glutamine, arginine, alpha-methyl-glutamic acid or is deleted;
X14 is aspartic acid, glutamic acid, leucine or is deleted;
X15 is phenylalanine or is deleted;
X16 is isoleucine, valine or is deleted;
X17 is alanine, cysteine, glutamic acid, glutamine, alpha-methyl-glutamic acid or is deleted;
X18 is tryptophan or is deleted;
X19 is alanine, isoleucine, leucine, valine or is deleted;
X20 is alanine, lysine, methionine, arginine or is deleted;
X21 is asparagine or is deleted;
X22 is threonine or is deleted;
X23 is cysteine, lysine or is deleted;
X24 is a peptide having 2 to 10 amino acids consisting of glycine or is deleted; and
R2 is KRNRNNIA (SEQ ID NO. 32), GPSSGAPPPS (SEQ ID NO. 33), GPSSGAPPPSK (SEQ ID NO. 34), HSQGTFTSDYSKYLD (SEQ ID NO. 35), HSQGTFTSDYSRYLDK (SEQ ID NO. 36), HGEGTFTSDLSKQMEEEAVK (SEQ ID NO. 37) or is deleted (excluded if the amino acid sequence of Formula 6 is identical to that of SEQ ID NO. 1).

More preferably, the peptide of the present invention may be selected from the group consisting of the peptides of SEQ ID NOs. 1 to 31. Much more preferably, the peptide of the present invention may be an oxyntomodulin derivative described in Table 1 of Example 2-1.

Oxyntomodulin has activities of two peptides, GLP-1 and glucagon. GLP-1 decreases blood glucose, reduces food intake, and suppresses gastric emptying, and glucagon increases blood glucose, facilitate lipolysis and decreases body-weight by increasing energy metabolisms. Different biological effects of two peptides can cause undesired effects like increasing blood glucose if glucagon shows more dominant effect than GLP-1, or causing nausea and vomiting if GLP-1 shows more dominant effect than glucagon. Therefore, the oxyntomodulin derivatives of the present invention are not only aimed to increase these activities, for example, amino acids at position 1 and 11 of oxyntomodulin which suppress the activity of glucagon, may be modified for balancing the activity ratios of glucagon and GLP-1.

The present inventors performed in vitro experiments to demonstrate that the peptide of the present invention shows excellent activities on the GLP-1 receptor and the glucagon receptor, compared to oxyntomodulin. Thus, it is suggested that the peptide of the present invention activates the GLP-1 receptor and the glucagon receptor to show more excellent therapeutic effects on obesity than the conventional oxyntomodulin. In addition, its inhibitory effects on in vivo food intake were examined, and it shows more excellent inhibitory effects on food intake than the conventional oxyntomodulin (FIG. 1).

It is apparent to those skilled in the art that when the oxyntomodulin derivatives of the present invention are modified using the typical techniques, including modification with polymers such as PEG and sugar chain or fusion with albumin, transferrin, fatty acid, and immunoglobulin in order to improve the therapeutic effects of the oxyntomodulin derivatives, they will show superior therapeutic effects to native oxyntomodulin. Therefore, the modified oxyntomodulin derivatives are also included in the scope of the present invention.

In another aspect, the present invention provides a polynucleotide encoding the peptide.

The term "homology", as used herein for the polynucleotide, indicates sequence similarity between wild-type amino acid sequences or wild-type nucleotide sequences, and includes a gene sequence that is 75% or higher, preferably 85% or higher, more preferably 90% or higher and even more preferably 95% or higher identical to the polynucleotide sequence encoding the peptide. The homology evaluation may be done with the naked eye or using a commercially available program. Using a commercially available computer program, the homology between two or more sequences may be expressed as a percentage (%), and the homology (%) between adjacent sequences may be evaluated. The polynucleotide encoding the peptide is inserted into a vector and expressed so as to obtain a large amount of the peptide.

In still another aspect, the present invention provides a pharmaceutical composition for the prevention or treatment of obesity comprising the peptide.

As used herein, the term "prevention" means all of the actions by which the occurrence of obesity is restrained or retarded by administration of the peptide or the composition, and the term "treatment" means all of the actions by which the symptoms of obesity have taken a turn for the better or been modified favorably by administration of the peptide or the composition.

As used herein, the term "administration" means introduction of an amount of a predetermined substance into a patient by a certain suitable method. The composition of the present invention may be administered via any of the common routes, as long as it is able to reach a desired tissue, for example, but is not limited to, intraperitoneal, intravenous, intramuscular, subcutaneous, intradermal, oral, topical, intranasal, intrapulmonary, or intrarectal administration. However, since peptides are digested upon oral administration, active ingredients of a composition for oral administration should be coated or formulated for protection against degradation in the stomach.

As used herein, the term "obesity" implies accumulation of an excess amount of adipose tissue in the body, and a body mass index (body weight (kg) divided by the square of the height (m)) above 25 is to be regarded as obesity. Obesity is usually caused by an energy imbalance, when the amount of dietary intake exceeds the amount of energy expended for a long period of time. Obesity is a metabolic disease that affects the whole body, and increases the risk for diabetes, hyperlipidemia, sexual dysfunction, arthritis, and cardiovascular diseases, and in some cases, is associated with incidence of cancer.

The pharmaceutical composition of the present invention may further include a pharmaceutically acceptable carrier, excipient, or diluent. As used herein, the term "pharmaceutically acceptable" means that the composition is sufficient to achieve the therapeutic effects without deleterious side effects, and may be readily determined depending on the type of the diseases, the patient's age, body weight, health conditions, gender, and drug sensitivity, administration route, administration mode, administration frequency, duration of treatment, drugs used in combination or coincident with the composition of this invention, and other factors known in medicine.

The pharmaceutical composition including the derivative of the present invention may further include a pharmaceutically acceptable carrier. For oral administration, the carrier may include, but is not limited to, a binder, a lubricant, a disintegrant, an excipient, a solubilizer, a dispersing agent, a stabilizer, a suspending agent, a colorant, and a flavorant. For injectable preparations, the carrier may include a buffering agent, a preserving agent, an analgesic, a solubilizer, an isotonic agent, and a stabilizer. For preparations for topical administration, the carrier may include a base, an excipient, a lubricant, and a preserving agent.

The composition of the present invention maybe formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single dosage form or a multidose container. The pharmaceutical composition may also be formulated into solutions, suspensions, tablets, pills, capsules and long-acting preparations.

On the other hand, examples of the carrier, the excipient, and the diluent suitable for the pharmaceutical formulations include lactose, dextrose, sucrose, sorbitol, mannitol, xylitol, erythritol, maltitol, starch, acacia rubber, alginate, gelatin, calciumphosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavorants, and antiseptics.

Further, the pharmaceutical composition of the present invention may have any formulation selected from the group consisting of tablets, pills, powders, granules, capsules, suspensions, liquids for internal use, emulsions, syrups, sterile aqueous solutions, non-aqueous solvents, lyophilized formulations and suppositories.

Further, the composition maybe formulated into a single dosage form suitable for the patient's body, and preferably is formulated into a preparation useful for peptide drugs according to the typical method in the pharmaceutical field so as to be administered by an oral or parenteral route such as through skin, intravenous, intramuscular, intra-arterial, intramedullary, intramedullary, intraventricular, pulmonary, transdermal, subcutaneous, intraperitoneal, intranasal, intracolonic, topical, sublingual, vaginal, or rectal administration, but is not limited thereto.

The peptide may be used by blending with a variety of pharmaceutically acceptable carriers such as physiological saline ororganicsolvents. In order to increase the stability or absorptivity, carbohydrates such as glucose, sucrose or dextrans, antioxidants such as ascorbic acid or glutathione, chelating agents, low molecular weight proteins or other stabilizers may be used.

The administration dose and frequency of the pharmaceutical composition of the present invention are determined by the type of active ingredient, together with various factors such as the disease to be treated, administration route, patient's age, gender, and body weight, and disease severity.

The total effective dose of the composition of the present invention may be administered to a patient in a single dose, or may be administered for a long period of time in multiple doses according to a fractionated treatment protocol. In the pharmaceutical composition of the present invention, the content of active ingredient may vary depending on the disease severity. Preferably, the total daily dose of the peptide of the present invention may be approximately 0.0001 μg to 500 mg per 1 kg of body weight of a patient. However, the effective dose of the peptide is determined considering various factors including patient's age, body weight, health conditions, gender, disease severity, diet, and secretion rate, in addition to administration route and treatment frequency of the pharmaceutical composition. In view of this, those skilled in the art may easily determine an effective dose suitable for the particular use of the pharmaceutical composition of the present invention. The pharmaceutical composition according to the present invention is not particularly limited to the formulation, and administration route and mode, as long as it shows the effects of the present invention.

The pharmaceutical composition of the present invention shows excellent in-vivo duration of efficacy and titer, thereby remarkably reducing the number and frequency of administration thereof.

Moreover, the pharmaceutical composition may be administered alone or in combination or coincident with other pharmaceutical formulations showing prophylactic or therapeutic effects on obesity. The pharmaceutical formulations showing prophylactic or therapeutic effects on obesity are not particularly limited, and may include a GLP-1 receptor agonist, a leptin receptor agonist, a DPP-IV inhibitor, a Y5 receptor antagonist, a Melanin-concentrating hormone (MCH) receptor antagonist, a Y2/3 receptor agonist, a MC3/4 receptor agonist, a gastric/pancreatic lipase inhibitor, a 5HT2c agonist, a β3A receptor agonist, an Amylin receptor agonist, a Ghrelin antagonist, and/or a Ghrelin receptor antagonist.

In still another aspect, the present invention provides a method for preventing or treating obesity, comprising the step of administering to a subject the peptide or the pharmaceutical composition including the same.

In the present invention, the term "subject" is those suspected of having obesity, which means mammals including human, mouse, and livestock having obesity or having the possibility of obesity. However, any subject to be treated with the peptide or the pharmaceutical composition of the present invention is included without limitation. The pharmaceutical composition including the peptide of the present invention is administered to a subject suspected of having obesity, thereby treating the subject effectively. The obesity is as described above.

The therapeutic method of the present invention may include the step of administering the composition including the peptide at a pharmaceutically effective amount. The total daily dose should be determined through appropriate medical judgment by a physician, and administered once or several times. With respect to the objects of the present invention, the specific therapeutically effective dose level for any particular patient may vary depending on various factors well known in the medical art, including the kind and degree of the response to be achieved, concrete compositions according to whether other agents are used therewith or not, the patient's age, body weight, health condition, gender, and diet, the time and route of administration, the secretion rate of the composition, the time period of therapy, other drugs used in combination or coincident with the composition of this invention, and like factors well known in the medical arts.

In still another aspect, the present invention provides a use of the peptide or the pharmaceutical composition including the same in the preparation of drugs for the prevention or treatment of obesity.

MODE FOR INVENTION

Hereinafter, the present invention will be described in more detail with reference to the following Examples. However, these Examples are for illustrative purposes only, and the invention is not intended to be limited by these Examples.

Example 1

Production of In Vitro Activated Cell Line

Example 1-1

Production of Cell Line Showing cAMP Response to GLP-1

PCR was performed using a region corresponding to ORF (Open Reading Frame) in cDNA (OriGene Technologies, Inc. USA) of human GLP-1 receptor gene as a template, and the following forward and reverse primers including each of the HindIII and EcoRI restriction sites so as to obtain a PCR product.

```
Forward primer:
                                      (SEQ ID NO. 47)
5'-CCCGGCCCCCGCGGCCGCTATTCGAAATAC-3'

Reverse primer:
                                      (SEQ ID NO. 48)
5'-GAACGGTCCGGAGGACGTCGACTCTTAAGATAG-3'
```

The PCR product was cloned into the known animal cell expression vector x0GC/dhfr to prepare a recombinant vector x0GC/GLP1R.

CHO DG44 cell line cultured in DMEM/F12 (10% FBS) medium was transfected with the recombinant vector x0GC/GLP1R using Lipofectamine (Invitrogen, USA), and cultured in a selection medium containing 1 mg/mL G418 and 10 nM methotraxate. Single clone cell lines were selected therefrom by a limit dilution technique, and a cell line showing excellent cAMP response to GLP-1 in a concentration-dependent manner was finally selected therefrom.

Example 1-2

Production of Cell Line Showing cAMP Response to Glucagon

PCR was performed using a region corresponding to ORF in cDNA (OriGene Technologies, Inc. USA) of human glucagon receptor gene as a template, and the following forward and reverse primers including each of the EcoRI and XhoI restriction sites so as to obtain a PCR product.

```
Forward primer:
                                      (SEQ ID NO. 49)
5'-CAGCGACACCGACCGTCCCCCCGTACTTAAGGCC-3'

Reverse primer:
                                      (SEQ ID NO. 50)
5'-CTAACCGACTCTCGGGGAAGACTGAGCTCGCC-3'
```

The PCR product was cloned into the known animal cell expression vector x0GC/dhfr to prepare a recombinant vector x0GC/GCGR.

CHO DG44 cell line cultured in DMEM/F12 (10% FBS) medium was transfected with the recombinant vector x0GC/GCGR using Lipofectamine, and cultured in a selection medium containing 1 mg/mL G418 and 10 nM methotraxate. Single clone cell lines were selected therefrom by a limit dilution technique, and a cell line showing excellent cAMP response to glucagon in a concentration-dependent manner was finally selected therefrom.

Example 2

Test on In Vitro Activity of Oxyntomodulin Derivatives

Example 2-1

Synthesis of Oxyntomodulin Derivatives

In order to measure in vitro activities of oxyntomodulin derivatives, oxyntomodulin derivatives having the following amino acid sequences were synthesized (Table 1).

TABLE 1

| Oxyntomodulin and oxyntomodulin derivatives | |
|---|---|
| SEQ ID NO. | Amino acid sequence |
| SEQ ID NO. 1 | HSQGTFTSDYSKYLDSRRAQDFVQWLMNTK RNRNNIA |
| SEQ ID NO. 2 | CA-SQGTFTSDYSKYLDEEAVRLFIEWLMNT KRNRNNIA |
| SEQ ID NO. 3 | CA-SQGTFTSDYSKYLDERRAQDFVAWLKNT GPSSGAPPPS |
| SEQ ID NO. 4 | CA-GQGTFTSDYSRYLEEEAVRLFIEWLKNG GPSSGAPPPS |
| SEQ ID NO. 5 | CA-GQGTFTSDYSRQMEEEAVRLFIEWLKNG GPSSGAPPPS |
| SEQ ID NO. 6 | CA-GEGTFTSDLSRQMEEEAVRLFIEWAAHSQ GTFTSDYSKYLD |
| SEQ ID NO. 7 | CA-SQGTFTSDYSRYLDEEAVRLFIEWLMNTK |
| SEQ ID NO. 8 | CA-SQGTFTSDLSRQLEEEAVRLFIEWLMNK |
| SEQ ID NO. 9 | CA-GQGTFTSDYSRYLDEEAVXLFIEWLMNT KRNRNNIA |
| SEQ ID NO. 10 | CA-SQGTFTSDYSRQMEEEAVRLFIEWLMNGG PSSGAPPPSK |
| SEQ ID NO. 11 | CA-GEGTFTSDLSRQMEEEAVRLFIEWAAHSQ GTFTSDYSRYLDK |
| SEQ ID NO. 12 | CA-SQGTFTSDYSRYLDGGGHGEGTFTSDLSK QMEEEAVK |
| SEQ ID NO. 13 | CA-SQGTFTSDYSRYLDXEAVXLFIEWLMNTK |
| SEQ ID NO. 14 | CA-GQGTFTSDYSRYLDEEAVXLFIXWLMNTK RNRNNIA |
| SEQ ID NO. 15 | CA-GQGTFTSDYSRYLDEEAVRLFIXWLMNTK RNRNNIA |
| SEQ ID NO. 16 | CA-SQGTFTSDLSRQLEGGGHSQGTFTSDLSR QLEK |
| SEQ ID NO. 17 | CA-SQGTFTSDYSRYLDEEAVRLFIEWIRNTK RNRNNIA |
| SEQ ID NO. 18 | CA-SQGTFTSDYSRYLDEEAVRLFIEWIRNGG PSSGAPPPSK |

TABLE 1-continued

Oxyntomodulin and oxyntomodulin derivatives

| SEQ ID NO. | Amino acid sequence |
|---|---|
| SEQ ID NO. 19 | CA-SQGTFTSDYSRYLDEEAVKLFIEWIRNTKRNRNNIA |
| SEQ ID NO. 20 | CA-SQGTFTSDYSRYLDEEAVKLFIEWIRNGGPSSGAPPPSK |
| SEQ ID NO. 21 | CA-SQGTFTSDYSRQLEEEAVRLFIEWVRNTKRNRNNIA |
| SEQ ID NO. 22 | DA-SQGTFTSDYSKYLDEKRAKEFVQWLMNTK |
| SEQ ID NO. 23 | HAibQGTFTSDYSKYLDEKRAKEFVCWLMNT |
| SEQ ID NO. 24 | HAibQGTFTSDYSKYLDEKRAKEFVQWLMNTC |
| SEQ ID NO. 25 | HAibQGTFTSDYSKYLDEKRAKEFVQWLMNTC |
| SEQ ID NO. 26 | HAibQGTFTSDYSKYLDEKRAKEFVQWLMNTC |
| SEQ ID NO. 27 | HAibQGTFTSDYSKYLDEQAAKEFICWLMNT |
| SEQ ID NO. 28 | HAibQGTFTSDYSKYLDEKRAKEFVQWLMNT |
| SEQ ID NO. 29 | CA-AibQGTFTSDYSKYLDEKRAKEFVQWLMNTC |
| SEQ ID NO. 30 | HAibQGTFTSDYAKYLDEKRAKEFVQWLMNTC |
| SEQ ID NO. 31 | YAibQGTFTSDYSKYLDEKRAKEFVQWLMNTC |

In Table 1, amino acids in bold and underlined represent ring formation, and amino acids represented by X mean a non-native amino acid, alpha-methyl-glutamic acid. In addition, CA represents 4-imidazoacetyl, and DA represents desamino-histidyl.

Example 2-2

Test on In Vitro Activity of Oxyntomodulin Derivatives

In order to measure anti-obesity efficacies of the oxyntomodulin derivatives synthesized in Example 2-1, cell activity was measured in vitro using the cell lines prepared in Examples 1-1 and 1-2.

The cell lines were those prepared by transfecting CHO (Chinese Hamster Ovary) to express human GLP-1 receptor gene and glucagon receptor gene, respectively. Thus, they are suitable to measure GLP-1 and glucagon activities. Therefore, the activity of each oxyntomodulin derivative was measured using each transformed cell line.

Specifically, each cell line was sub-cultured twice or three time a week, and aliquoted in each well of a 96-well plate at a density of 1×10$^5$, followed by cultivation for 24 hours.

The cultured cells were washed with KRB buffer and suspended in 40 ml of KRB buffer containing 1 mM IBMX, and left at room temperature for 5 minutes. Oxyntomodulin (SEQ ID NO. 1) and oxyntomodulin derivatives (represented by SEQ ID NOs. 2-6, 8, 10-13, 17, 18, 23-25, 27-30 and 31) were diluted from 1000 nM to 0.02 nM by 5-fold serial dilution, and each 40 mL thereof was added to the cells, and cultured at 37° C. for 1 hour in a CO2 incubator. Then, 20 mL of cell lysis buffer was added for cell lysis, and the cell lysates were applied to a cAMP assay kit (Molecular Device, USA) to measure cAMP concentrations. $EC_{50}$ values were calculated therefrom, and compared to each other. $EC_{50}$ values are shown in the following Table 2.

TABLE 2

Comparison of in vitro activities for GLP-1 receptor and glucagon receptor between oxyntomodulin and oxyntomodulin derivatives

| SEQ ID NO. | $EC_{50}$ (nM) | |
|---|---|---|
| SEQ ID NO. | CHO/GLP-1R | CHO/GCGR |
| SEQ ID NO. 1 | 50-210 | 10-43 |
| SEQ ID NO. 2 | 51.8 | 12.8 |
| SEQ ID NO. 3 | >1,000 | 637.7 |
| SEQ ID NO. 4 | 5.5 | >1,000 |
| SEQ ID NO. 5 | 5.9 | >1,000 |
| SEQ ID NO. 6 | 500.1 | >1,000 |
| SEQ ID NO. 8 | 419.6 | >1,000 |
| SEQ ID NO. 10 | >1,000 | >1,000 |
| SEQ ID NO. 11 | >1,000 | >1,000 |
| SEQ ID NO. 12 | >1,000 | >1,000 |
| SEQ ID NO. 13 | >1,000 | >1,000 |
| SEQ ID NO. 17 | 97.9 | >1,000 |
| SEQ ID NO. 18 | 96.3 | >1,000 |
| SEQ ID NO. 23 | 2.46 | 5.8 |
| SEQ ID NO. 24 | 1.43 | 6.95 |
| SEQ ID NO. 25 | 1.9 | 1.3 |
| SEQ ID NO. 27 | 2.8-5.5 | 3.1-5.6 |
| SEQ ID NO. 28 | 3.1 | 0.3 |
| SEQ ID NO. 29 | 14.25 | 17.3 |
| SEQ ID NO. 30 | 2.20 | 80.2 |
| SEQ ID NO. 31 | 12.5 | 1.0 |

As shown in Table 2, there were oxyntomodulin derivatives showing excellent in vitro activities and different ratios of activities on GLP-1 receptor and glucagon receptor, compared to native oxyntomodulin of SEQ ID NO. 1.

It is known that oxyntomodulin activates both the GLP-1 receptor and glucagon receptor to suppress appetite, facilitate lipolysis, and promote satiety, thereby showing anti-obesity effects. The oxyntomodulin derivatives according to the present invention show higher in vitro activities on both the GLP-1 receptor and glucagon receptor than the wild-type oxyntomodulin, and therefore can be used as a therapeutic agent for obesity with higher efficacies than the known oxyntomodulin.

Example 3

Test on In Vivo Activity of Oxyntomodulin Derivatives

In order to measure in vivo therapeutic activity of oxyntomodulin derivatives, changes in food intake by administration of oxyntomodulin derivatives were examined in ob/ob mouse using native oxyntomodulin as a control.

Specifically, obese diabetic ob/ob mice, commonly used to test the efficacies of therapeutic agents for obesity and diabetes, were fasted for 16 hours, and administered with 1 or 10 mg/kg of oxyntomodulin, or 0.02, 0.1, 1 or 10 mg/kg of the oxyntomodulin derivative of SEQ ID NO. 2. Then, food intake was examined for 2 hours (FIG. 1). FIG. 1 is a graph showing changes in food intake according to administration dose of oxyntomodulin or oxyntomodulin derivative. As shown in FIG. 1, administration of 1 mg/kg of oxyntomodulin derivative showed more excellent inhibitory effects on food intake than administration of 10 mg/kg of oxyntomodulin.

Taken together, the oxyntomodulin derivatives of the present invention have much higher anti-obesity effects than the wild-type oxyntomodulin, even though administered at a lower dose, indicating improvement in the problems of the wild-type oxyntomodulin that shows lower anti-obesity effects and should be administered at a high dose three times a day.

The invention claimed is:

1. A peptide comprising the amino acid sequence of SEQ ID NO:24, SEQ ID NO:25, SEQ ID NO:26, or SEQ ID NO:28.

2. The peptide according to claim 1, wherein Glu at position 16 and Lys at position 20, taken together, form a ring.

3. The peptide according to claim 1, wherein Lys at position 12 and Glu at position 16, taken together, form a ring.

4. A pharmaceutical composition comprising the peptide of claim 1 as an active ingredient and a pharmaceutically acceptable carrier.

5. The pharmaceutical composition according to claim 4, wherein the composition is administered alone or in combination or coincident with other pharmaceutical formulations, wherein said other pharmaceutical formulation is selected from the group consisting of a glucagon like peptide-1 receptor agonist, a leptin receptor agonist, a dipeptidyl peptidase-IV inhibitor, a Y5 receptor antagonist, a Melanin-concentrating hormone receptor antagonist, a Y2/3 receptor agonist, a MC3/4 receptor agonist, a gastric/pancreatic lipase inhibitor, a 5HT2c agonist, a β3A receptor agonist, an Amylin receptor agonist, a Ghrelin antagonist, and a Ghrelin receptor antagonist.

6. A pharmaceutical composition comprising the peptide of claim 2 as an active ingredient and a pharmaceutically acceptable carrier.

7. The pharmaceutical composition according to claim 6, which further comprises another active ingredient selected from the group consisting of a glucagon like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, and a ghrelin receptor antagonist.

8. A pharmaceutical composition comprising the peptide of claim 3 as an active ingredient and a pharmaceutically acceptable carrier.

9. The pharmaceutical composition according to claim 8, which further comprises another active ingredient selected from the group consisting of a glucagon like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, and a ghrelin receptor antagonist.

10. A method for inhibiting or treating obesity, comprising administering to a subject in need thereof the peptide of claim 1.

11. The method of claim 10, which further comprises administering another active ingredient selected from the group consisting of a glucagon like peptide-1 receptor agonist, a leptin receptor agonist, a dipeptidyl peptidase-IV inhibitor, a Y5 receptor antagonist, a Melanin-concentrating hormone receptor antagonist, a Y2/3 receptor agonist, a MC3/4 receptor agonist, a gastric/pancreatic lipase inhibitor, a 5HT2c agonist, a β3A receptor agonist, an Amylin receptor agonist, a Ghrelin antagonist, and a Ghrelin receptor antagonist.

12. A method for inhibiting or treating obesity, comprising administering to a subject in need thereof the composition of claim 4.

13. The method of claim 12, which further administering another pharmaceutical formulation, wherein said other pharmaceutical formulation is selected from the group consisting of a glucagon like peptide-1 receptor agonist, a leptin receptor agonist, a dipeptidyl peptidase-IV inhibitor, a Y5 receptor antagonist, a Melanin-concentrating hormone receptor antagonist, a Y2/3 receptor agonist, a MC3/4 receptor agonist, a gastric/pancreatic lipase inhibitor, a 5HT2c agonist, a β3A receptor agonist, an Amylin receptor agonist, a Ghrelin antagonist, and a Ghrelin receptor antagonist.

14. A method for treating obesity, comprising administering to a subject in need thereof the composition of claim 6.

15. The method of claim 14, which further comprises administering another active ingredient selected from the group consisting of a glucagon like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, and a ghrelin receptor antagonist.

16. A method for treating obesity, comprising administering to a subject in need thereof the composition of claim 8.

17. The method of claim 16, which further comprises administering another active ingredient selected from the group consisting of a glucagon like peptide-1 receptor agonist, a leptin receptor agonist, a dipeptidyl peptidase-IV inhibitor, a Y5 receptor antagonist, a melanin-concentrating hormone receptor antagonist, a Y2/3 receptor agonist, a MC3/4 receptor agonist, a gastric/pancreatic lipase inhibitor, a 5HT2c agonist, a β3A receptor agonist, an amylin receptor agonist, a ghrelin antagonist, and a ghrelin receptor antagonist.

* * * * *